US 8,353,815 B2
Jan. 15, 2013

(12) United States Patent
Okada

(54) INSTRUMENT FOR AN ENDOSCOPE

(75) Inventor: Tsutomu Okada, Tokyo (JP)

(73) Assignee: Olympus Corporation, Tokyo (JP)

(*) Notice: Subject to any disclaimer, the term of this patent is extended or adjusted under 35 U.S.C. 154(b) by 566 days.

(21) Appl. No.: 11/446,995

(22) Filed: Jun. 5, 2006

(65) Prior Publication Data

US 2006/0224041 A1 Oct. 5, 2006

Related U.S. Application Data

(63) Continuation of application No. PCT/JP2005/001409, filed on Feb. 1, 2005.

(30) Foreign Application Priority Data

Feb. 6, 2004 (JP) ................................ P2004-030651

(51) Int. Cl.
*A61B 1/00* (2006.01)

(52) U.S. Cl. ........ 600/104; 600/102; 600/106; 600/131; 600/153

(58) Field of Classification Search .................. 600/102, 600/104, 131, 153–159, 136; 604/159, 165.01, 604/174
See application file for complete search history.

(56) References Cited

U.S. PATENT DOCUMENTS

| | | | | |
|---|---|---|---|---|
| 5,150,715 A * | 9/1992 | Ishiguro et al. | ............... | 600/463 |
| 5,820,546 A | 10/1998 | Ouchi | | |
| 5,846,183 A * | 12/1998 | Chilcoat | ..................... | 600/136 |
| 5,904,647 A * | 5/1999 | Ouchi | ......................... | 600/104 |
| 5,931,833 A * | 8/1999 | Silverstein | ..................... | 606/1 |
| 6,004,263 A * | 12/1999 | Nakaichi et al. | ............... | 600/176 |
| 6,203,533 B1 | 3/2001 | Ouchi | | |
| 6,273,882 B1 * | 8/2001 | Whittier et al. | ................... | 606/1 |
| 6,743,185 B2 * | 6/2004 | Weber et al. | .................. | 600/564 |
| 7,179,223 B2 * | 2/2007 | Motoki et al. | ................. | 600/131 |
| 7,198,599 B2 * | 4/2007 | Goto et al. | .................... | 600/154 |
| 7,220,227 B2 * | 5/2007 | Sasaki et al. | .................. | 600/154 |
| 2004/0015050 A1 | 1/2004 | Goto et al. | | |
| 2005/0065399 A1 * | 3/2005 | Sasaki et al. | .................. | 600/106 |
| 2005/0070754 A1 * | 3/2005 | Nobis et al. | ..................... | 600/16 |

FOREIGN PATENT DOCUMENTS

| | | |
|---|---|---|
| JP | H1-165006 | 11/1989 |
| JP | H02-224651 | 9/1990 |
| JP | H3-53211 | 5/1991 |
| JP | 9-94253 | 4/1997 |
| JP | h11-76244 | 3/1999 |
| JP | 2002-330973 | 11/2002 |
| JP | 2004-49891 | 2/2004 |

OTHER PUBLICATIONS

JP Office Action dated Nov. 24, 2009 with English-language translation.

* cited by examiner

*Primary Examiner* — Matthew J Kasztejna
(74) *Attorney, Agent, or Firm* — Scully, Scott, Murphy & Presser, P.C.

(57) ABSTRACT

An instrument for an endoscope includes an insertion portion inserted into an instrument insertion channel of the endoscope, and a pair of biopsy cups provided at the distal end of the insertion portion so as to be able to be openable and closable. Also, an operation portion for operating the paired biopsy cups is provided at the proximal end of the insertion portion. The operation portion is provided with a hook, and an engaged member engageable with the hook is attached to a part protruding out from the endoscope, of the insertion portion.

9 Claims, 13 Drawing Sheets

INSTRUMENT FOR AN ENDOSCOPE

PRIORITY CLAIM

This application is continuation application of a PCT Application No. PCT/JP2005/001409, filed on Feb. 1, 2005, entitled "INSTRUMENT FOR AN ENDOSCOPE" whose priority is claimed on Japanese Patent Application No. 2004-030651 filed on Feb. 6, 2004. The description thereof is incorporated herein by reference.

BACKGROUND OF THE INVENTION

1. Field of the Invention

The present invention relates to an instrument for an endoscope, which is used after being inserted into a channel of an endoscope.

2. Description of Related Art

In order to carry out inspection and therapy of a human body, a method has been known in which a predetermined living body tissue is biopsied by inserting an instrument such as a biopsy forceps, a cytological diagnosis brush or the like into a channel of an endoscope when sampling a living body tissue or the like in a body cavity.

Herein, where the biopsy forceps is used, a biopsy cup that composes a forceps portion is opened and closed by operating an operation portion outside a human body, and a living body tissue is picked up therewith. The forceps portion is retracted with the living body tissue therein, and the living body tissue held in the biopsy cup is peeled off from the other living body tissue in a human body and is collected (for example, refer to Japanese Unexamined Patent Application, First Publication No. H11-76244).

Also, where a cytological diagnosis brush is used, the brush portion is projected from the distal end of a flexible sheath by operating the operation portion outside the human body. By causing the brush portion to extend and retract along with the sheath, the tunica mucosa is abraded, and tissues peeled off by abrasion are collected along with the brush portion (for example, refer to Japanese Unexamined Patent Application, First Publication No. H02-224651).

SUMMARY OF THE INVENTION

The present invention provides an instrument for an endoscope, including an insertion portion inserted into the channel of an endoscope, a treatment portion for treating a target region, provided at the distal end of the insertion portion, an operation portion for operating the treatment portion, provided at the proximal end of the insertion portion, and an engaging device which allows a part of the insertion portion protruding out from the endoscope to engage with the operation portion.

In the instrument for an endoscope according to the present invention, it is preferable that the operation portion be provided with a holding portion held by fingers of an operator, and the engaging device be provided on the distal side of the insertion portion from the gripping portion.

In the instrument for an endoscope according to the present invention, it is preferable that the engaging device be provided with a hook secured in the insertion portion or the operation portion and engaged member on which the hook is engaged.

In the instrument for an endoscope according to the present invention, it is preferable that the engaging device include first engaging device provided in either one of the insertion portion and the operation portion and having a notched section, in which the insertion portion is fitted, formed therein, and second engaging device provided in the other one thereof, and having a large-diameter portion, the diameter of which is larger than the width of the notched section, formed therein.

In the instrument for an endoscope according to the present invention, it is preferable that the engaging device be a gripping member for gripping the insertion portion or the operation portion.

In the instrument for an endoscope according to the present invention, it is preferable that the engaging device allow the part of the insertion portion to engage with the operation portion so that the insertion portion and the operation portion cross each other.

In the instrument for an endoscope according to the present invention, it is preferable that the treatment portion be provided with a pair of biopsy cups between which a living body tissue may be gripped, and brush portions for abrading the living body tissue.

DESCRIPTION OF THE PREFERRED EMBODIMENTS

Hereinafter, a description is given of preferred embodiments of the present invention with reference to the accompanying drawings.

First, a description is given of a first embodiment of an instrument for an endoscope according to the present invention with reference to FIG. 1 through FIG. 6.

Figure 1:
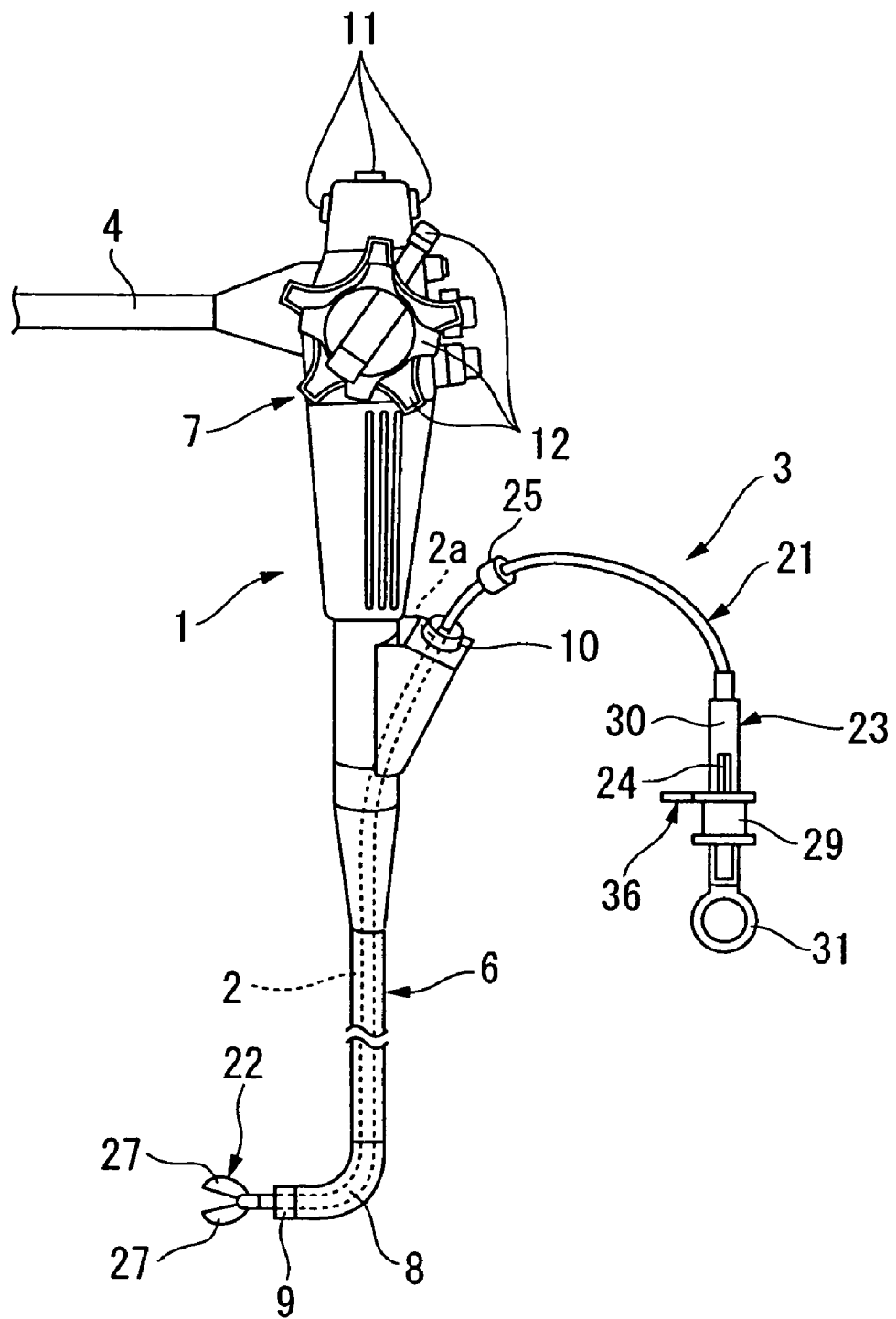
FIG. 1 is a view depicting a state where an instrument for an endoscope is inserted into its insertion portion.

The instrument for an endoscope according to the present embodiment includes, as depicted in FIG. 1, an endoscope 1, an instrument 3 for an endoscope (hereinafter called an instrument) which is inserted into an instrument inserting channel 2 of the endoscope 1, and a control unit (not illustrated) connected to the endoscope 1 via a universal cord 4. The control unit includes devices for processing and displaying images picked up by using the endoscope 1 and a light source for illumination for photographing.

The endoscope 1 is provided with an insertion portion 6 to be inserted into a human body and an operation portion 7 connected to the proximal end (outside-body) of the insertion portion 6. The insertion portion 6 has flexibility, because of which the insertion portion 6 can be easily inserted into a human body. The distal end of the insertion portion 6 is provided with a curved portion 8 whose angular direction is variable. A distal end cover 9 is secured at the distal end of the curved portion 8. A pickup portion for observing an internal state and a light projection portion for projecting illumination light are built into the distal end cover 9. An opening of the instrument insertion channel 2 is formed in the distal end face of the distal end cover 9, and a forceps port 2a of the instrument insertion channel 2 is formed in the operation portion 7, the instrument insertion channel 2 being caused to communicate with the opening and the forceps port 2a which are formed at the distal end face of the distal end cover 9. The forceps port 2a is provided with a forceps plug 10 so as to cover the forceps port 2a.

The operation portion 7 is provided with a plurality of switches 11 and a plurality of operation knobs 12 in addition to the forceps port 2a. A switch for recording images picked up by the pickup portion and a switch for switching illumination on and off are available as the switches 11. Signals of the respective switches 11 are transmitted to the control unit via the universal cord 4. Also, a knob for changing the direction of the curved portion 8 to a predetermined direction and a knob for maintaining the angle of the curved portion 8, when its direction is changed, are available as the operation knobs 12.

Figure 2:
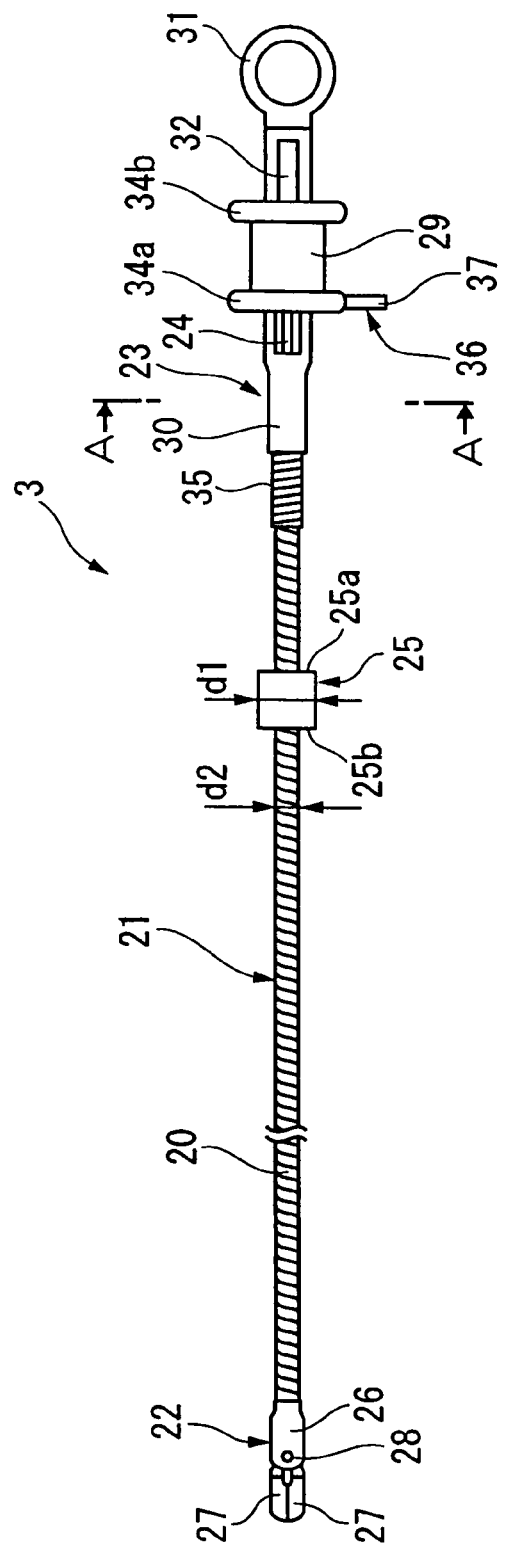
FIG. 2 is a view depicting a configuration of the instrument for an endoscope.

As depicted in FIG. 2, the instrument 3 is a biopsy forceps. The instrument 3 includes an insertion portion 21 to be inserted into the instrument insertion channel 2 (refer to FIG. 1), a treatment portion 22 secured at the distal end of the insertion portion 21, an operation portion (handle) 23 secured at the proximal end of the insertion portion 21 for operation of the treatment portion 22, etc., and an operation wire 24 passing from the treatment portion 22 through the insertion portion 21 and being drawn out to the operation portion 23.

The insertion portion 21 is covered with a flexible sheath 20. The sheath 20 is a metal or plastic coil sheath. An engaged member 25 to be described later is attached on the proximal side of the insertion portion 21.

The treatment portion 22 includes a supporting member (distal end cover) 26 fixed at the distal end of the insertion portion 21. A pair of biopsy cups 27 disposed so as to be opposed to each other are rotatably supported by a support axis 28 at the distal end of the supporting member 26. The respective biopsy cups 27 are shaped to be bowl-like and are linked with one end of a link mechanism (not illustrated) provided in the supporting member 26. The other end of the link mechanism is connected to the operation wire 24, and if the operation wire 24 is extended and retracted, the paired biopsy cups 27 are turned about the support axis 28.

The operation wire 24 is inserted into the supporting member 26 and the insertion portion 21 so as to extend and retract therein from one end thereof, which is connected to the other end of the link mechanism of the treatment portion 22, and the other end thereof, which is connected to a slider (holding portion), in which fingers of an operator are placed, at the operation portion 23.

The operation portion 23 includes an operation portion body 30, in which the proximal end of the insertion portion 21 is fixed, at the distal end thereof. The slider 29 is slidably attached to the operation portion body 30.

Figure 3:
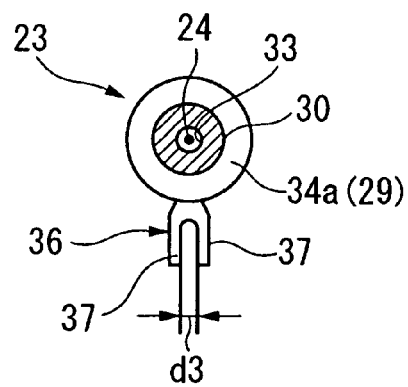
FIG. 3 is a sectional view taken along line A-A of FIG. 2.

The operation portion body 30 is shaped to be slender, and the diameter at the proximal end thereof is made larger than that of the distal end thereof. A finger-hook ring 31 is attached to the proximal end of the operation portion body 30. Also, a slit 32 is provided along the length of the operation portion body 30 at the diameter-enlarged section between the proximal end of the operation portion body 30 and the distal end thereof. The slit 32 runs through the operation portion body 30 across its diameter. Further, as depicted in FIG. 2 and FIG. 3, an insertion hole 33 in which the operation wire 24 is inserted so as to be extended and retracted is formed between the slit 32 and the distal end face of the operation portion body 30.

As depicted in FIG. 2, the slider 29 is made of a cylindrical member slidably fitted in the operation portion body 30 along the slit 32. A flange portion 34a and a flange portion 34b whose outer diameters are larger than that of the slider 29 are provided at the distal end and the proximal end of the slider 29. Also, as described above, the other end of the operation wire 24 is fixed at the slider 29. A protection member 35 which covers the outer surface of the insertion portion 21 is attached to the distal end of the operation portion body 30. The protection member 35 prevents the insertion portion 21 from being folded in the vicinity of the point fixed with the operation portion 23 when the operation portion 23 is operated.

Engaging devices for engaging the insertion portion 21 with the operation portion 23 are attached to the insertion portion 21 and the operation portion 23, respectively. The engaging device (the second engaging member) at the insertion portion 21 side is an engaged member 25 attached to the portion protruding out from the endoscope 1 (refer to FIG. 1) of the insertion portion 21. The engaged member 25 is a large-diameter portion which has a larger diameter d1 than the outer diameter d2 of the insertion portion 21. The engaging device (the first engaging device) at the operation portion 23 side is a hook 36 attached to the flange portion 34a secured on the distal side of the slider 29. The hook 36 is provided so as to extend from the slider 29 directly outward. As depicted in FIG. 3, the distal end of the hook 36 is notched, and is formed to be roughly U-shaped, with two engaging pieces 37 arrayed. The size of the notch, that is, the gap d3 between the two engaging pieces 37 is larger than the outer diameter d2 of the insertion portion 21 but is smaller than the outer diameter d1 of the engaged member 25.

Next, a description is given of how to use the instrument 3. First, the insertion portion 6 of the endoscope 1 depicted in FIG. 1 is inserted into a body cavity of a patient. Next, the instrument 3 is inserted into the instrument insertion channel 2 of the endoscope 1 from the distal end. With reference to internal images picked up by the pickup portion of the endoscope 1, the instrument 3 is projected from the distal end of the insertion portion 6 of the endoscope 1 to the vicinity of living body tissue to be sampled.

Figure 4:
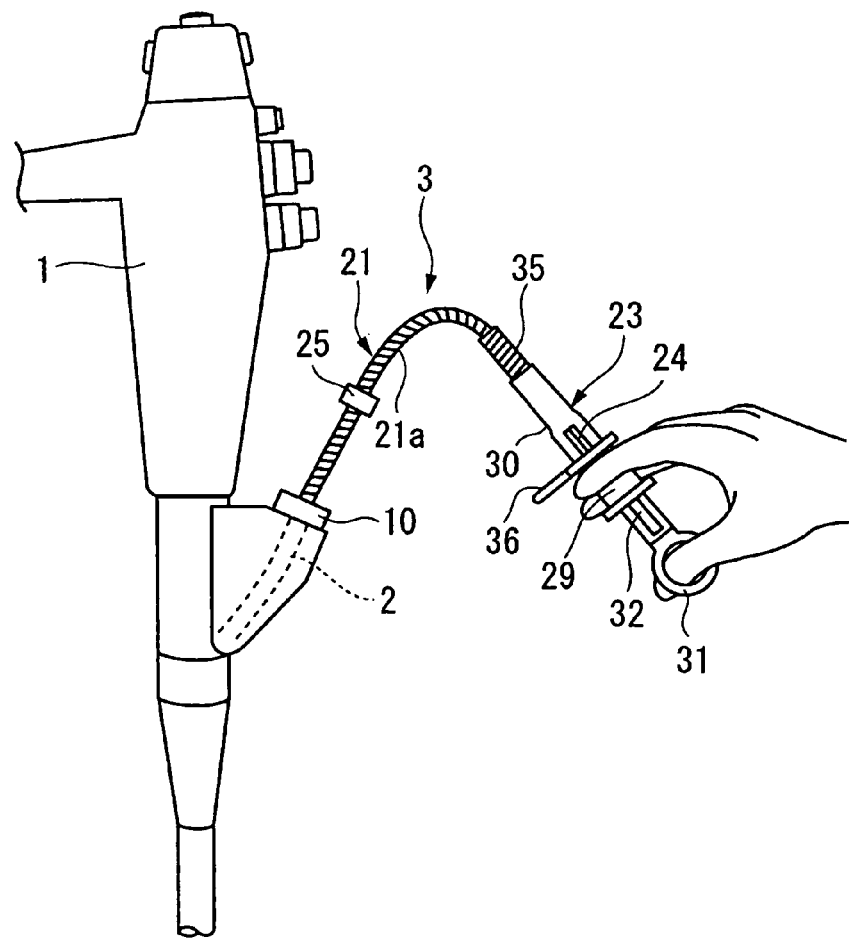
FIG. 4 is a view depicting operation of the instrument for an endoscope.

When the instrument 3 approaches the vicinity of living body tissue to be sampled thereby, an operator places his/her thumb in the finger-hook ring 31, grips the slider 29 with his/her index finger and middle finger, and holds the operation portion 23 as depicted in FIG. 4. A pair of biopsy cups 27 are opened and closed by extending and retracting the slider 29 and a predetermined living body tissue is caught by the biopsy cups 27. In detail, the slider 29 is extended to the distal end of the operation portion 23 and the operation wire 24 is pushed into the insertion portion 21, whereby, as depicted in FIG. 2, since one end of the internal link mechanism of the treatment portion 22 is pushed into the distal end by the operation wire 24, the link mechanism is driven and the paired biopsy cups 27 open about the support axis 28.

Figure 5:
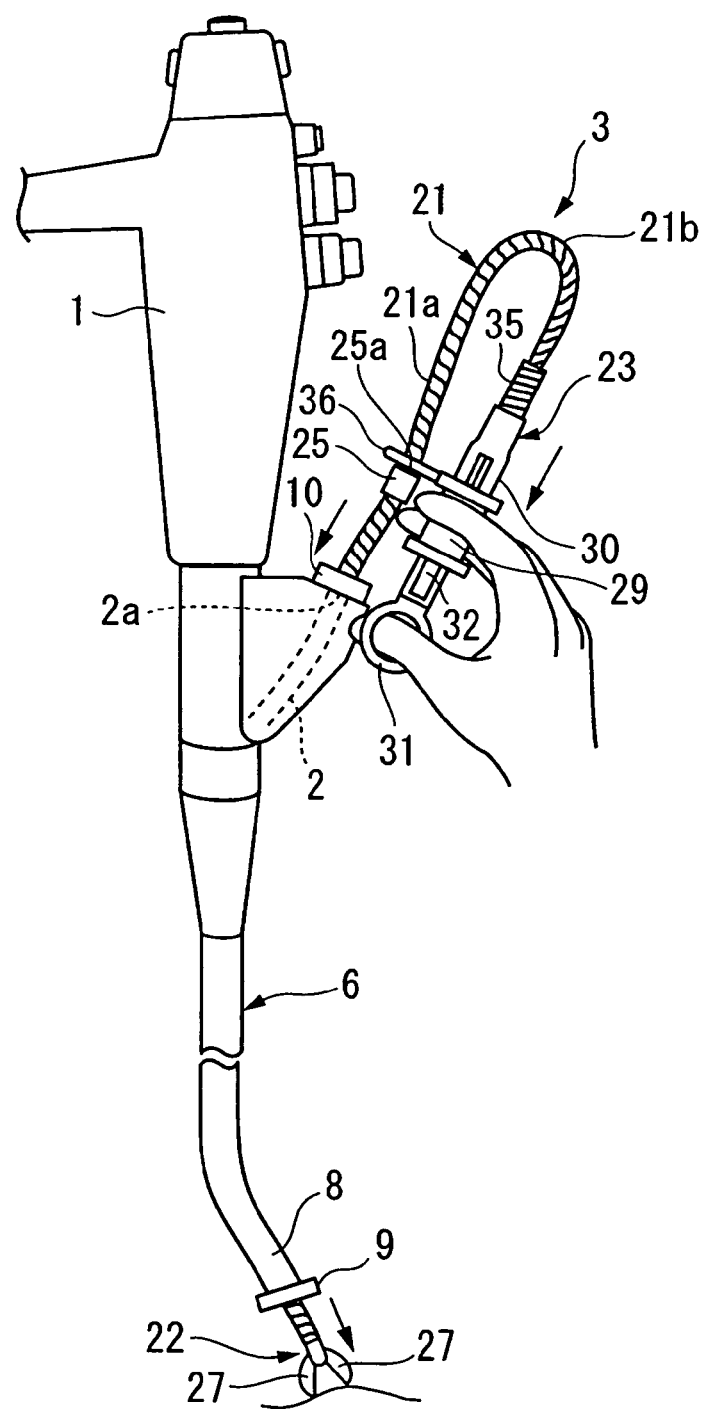
FIG. 5 is a view depicting operation of the instrument for an endoscope, and depicts an engaged state when the insertion portion is extended.

After the paired biopsy cups 27 are opened, as depicted in FIG. 5, the hook 36 catches on the insertion portion 21 at the operation portion 23 side from the engaged member 25, and the hook 36 is engaged with the proximal end side face 25a of the engaged member 25. Further, the operation portion 23 is moved so as to approach the forceps port 2a along the insertion portion 21 to push into the insertion channel 2, wherein the biopsy cups 27 are pushed into the living body tissue. After that, by causing the slider 29 to retract, the operation wire 24 can be pulled toward the other end of the link mechanism, whereby the biopsy cups 27 are closed to catch the living body tissue.

After the living body tissue is caught by the paired biopsy cups 27, the engagement position of the hook 36 with the engaged member 25 is changed. That is, the hook 36 is engaged with the distal side face 25b of the engaged member 25. In a state where the hook 36 is engaged with the engaged member 25, the operation portion 23 is pulled up so that the hook 36 is distanced from the forceps port 2a of the instrument insertion channel 2. Thereby, the insertion portion 21 is taken out from the instrument insertion channel 2 along with the engaged member 25 in response to the amount of movement of the operation portion 23. That is, since the instrument 3 is moved so as to be pulled out from the endoscope 1, the treatment portion 22 is moved so as to retract toward the endoscope 1 as depicted in FIG. 2, and the living body tissue caught by the paired biopsy cups 27 is torn. After the living body tissue is torn, the instrument 3 is removed from the instrument insertion channel 2 to collect the living body tissue.

Figure 6:
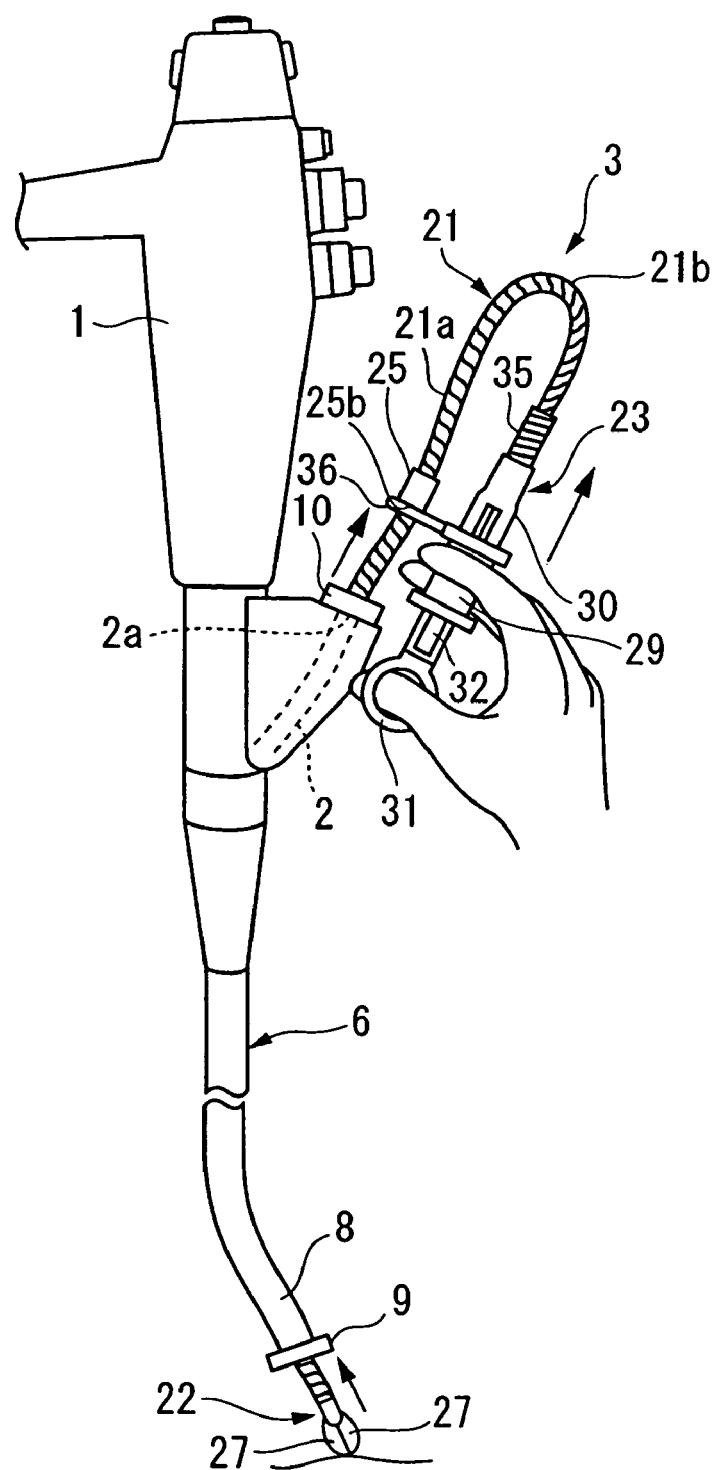
FIG. 6 is a view depicting operation of the instrument for an endoscope, and depicts an engaged state when the insertion portion is retracted.

According to the present embodiment, as depicted in FIG. 5 and FIG. 6, since the engaged member 25 is attached to the portion protruding out from the endoscope 1 of the insertion portion 21, that is, to the section 21a from the forceps port 2a of the instrument insertion channel 2 to the operation portion 23, and the hook 36 engagable with the engaged member 25 is provided in the operation portion 23, it becomes possible to push the treatment portion 22 into the living body tissue and to pull back the treatment portion 22 to the outside of the body by changing the direction of engagement without directly gripping the insertion portion 21. Therefore, the operator becomes able to open and close or extend and retract the biopsy cups 27 without the assistance of an assistant. In addition, since the hook 36 is attached to the flange portion 34a on the distal side of the slider 29, it becomes possible to cause the treatment portion 22 with the insertion portion 21 on the distal side from the position where the operation portion 23 is held. Accordingly, the biopsy cups 27 can be opened and closed or extended and retracted by way of natural actions. Further, since a force of pulling the insertion portion 21 is concentrated at the place where the hook 26 is caught, that is, the engaged member 25, it is possible to efficiently pull back the insertion portion 21, and a predetermined living body tissue can be easily sampled.

Further, since there is no need to simultaneously grip the operation portion 23 and the insertion 21 with the hands, the insertion portion 21 is prevented from being excessively bent even where the operation portion 23 is inverted, and it is possible to prevent stress from being concentrated at a part 21b (refer to FIG. 5) where the insertion portion 21 is bent. Also, it is preferable that the position of attachment the engaged member 25 be a position close to the forceps port 2a of the instrument insertion channel 2 on a part 21a protruding out from the endoscope 1. If it is, when the hook 36 is engaged with the engaged member 25, it becomes possible to further reduce the load applied onto the part 21b where the insertion portion 21 is bent.

Figure 7:
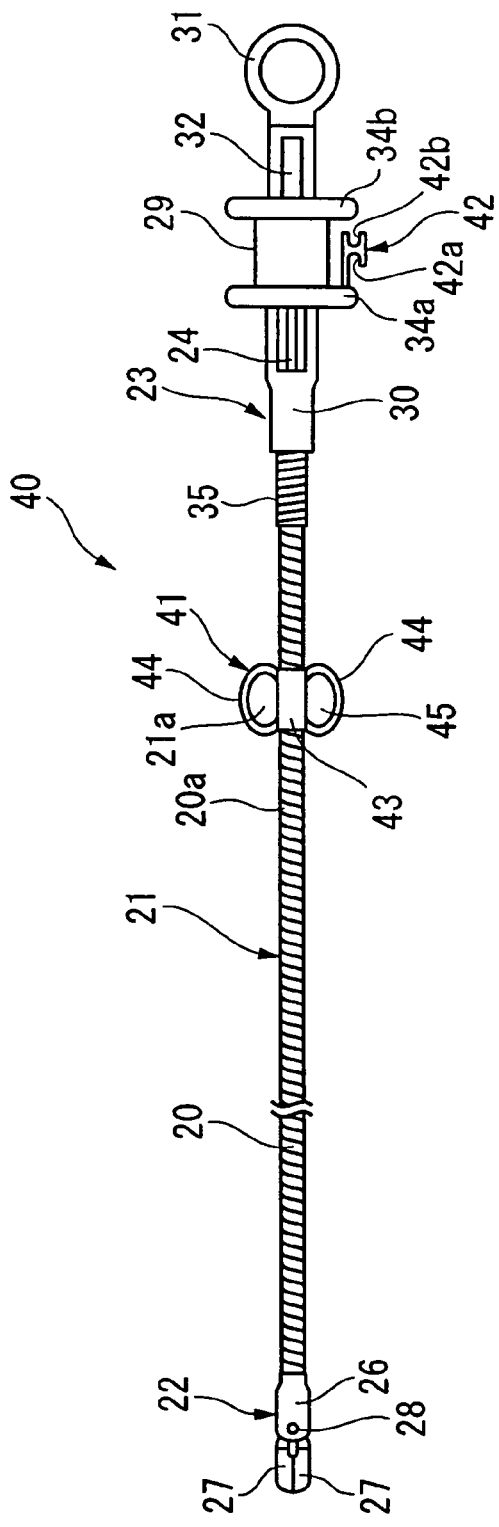
FIG. 7 is a view depicting a configuration of the instrument for an endoscope.

Next, a description is given of a second embodiment of an instrument for an endoscope according to the present invention with reference to FIG. 7. Components which are identical to those of Embodiment 1 are given the same reference numerals, and redundant description thereof is omitted.

As depicted in FIG. 7, the instrument 40 has a flexible insertion portion 21. The distal end of the insertion portion 21 is provided with a treatment portion 22 equipped with a pair of biopsy cups 27. Further, an operation portion 23 is provided at the proximal end of the insertion portion 21.

The engaging device of this embodiment includes an engaged member 41 secured at the portion 21a protruding out from the endoscope 1, of the insertion portion 21, and a hook 42 that is an engaging member attached to the operation portion 23. The engaged member 41 has a cylindrical body 43 covering the insertion portion 21 and catching portions 44 fixed on the cylindrical body 43. The two catching portions 44 are attached one by one to positions offset by 180° from each other with respect to the cylindrical body 43. Further, a through-hole 45 is formed in each of the catching portions 44 in the direction roughly orthogonal to the length of the insertion portion 21.

One end of the hook 42 is fixed at the flange portion 34a on the distal side of the slider 29, and extends from one end thereof toward the proximal end (toward the finger-hook ring 31) of the operation portion body 30. Two notches 42a and 42b are formed in the hook 42 extending parallel to the length of the operation portion 23, and the hook 42 is roughly H-shaped. In addition, the notch 42a has an end opening toward the distal end of the operation portion 23, and the notch 42b has an end opening toward the proximal end (toward the finger-hook ring 31) of the operation portion 23. The widths of the respective notches 42a and 42b are larger than the thickness and width of the ring of the catching portions 44.

After the instrument 40 is inserted into the insertion channel 2 when operating the instrument 40 and the paired biopsy cups 27 are opened by operating the operation portion 23, the insertion portion 21 is engaged with the operation portion 23 toward the distal end. That is, the open end of the notch 42b of the hook 42 is turned toward the distal end of the insertion portion 21, and the hook 42 is engaged with the catching portion 44 from the inside of the through-hole 45 toward the distal end. In this state, the operation portion 35 is moved so that the hook 42 approaches the forceps port 2a, and the insertion portion 3 is pushed in to press the biopsy cups 27 against a living body tissue.

As the slider 29 is pulled back, the paired biopsy cups 27 are closed, the living body tissue is caught between the cups 27, and the hook 42 and the engaged member 41 are engaged with each other toward the proximal end of the insertion portion 21. That is, the open end of the notch 42a of the hook 42 is turned toward the proximal end of the insertion portion 21, and the hook 42 is engaged with the catching portion 44 from the inside of the through-hole 45 toward the proximal end. In this state, as the operation portion 23 is moved in the direction along which the hook 42 is pulled apart from the insertion port (refer to FIG. 1) of the endoscope 1, the insertion portion 21 is pulled via the hook 42, and the insertion portion 21 is pulled back from the endoscope 1 in response to the amount of movement of the operation portion 23, so that the treatment portion 22 in the living body is retracted, and the living body tissue caught between the paired biopsy cups 27 is torn.

In the present embodiment, since the catching portion 44 is provided in the section 21a from the forceps port 2a of the instrument insertion channel 2 of the insertion portion 21 to the operation portion 23, and the hook 42 is provided at the flange portion 34a of the operation portion 23, the treatment portion 22 can be extended toward the living body tissue by changing the engagement direction without directly gripping the insertion portion 21, and the treatment portion 22 can be pulled back outside a human body. Accordingly, the operator becomes able to open and close or extend and retract the biopsy cups 27 by way of natural actions.

Also, the through-hole 45 of the catching portion 44 may be formed so as to be parallel to the lengthwise direction of the insertion portion 21. Also, the shape of the catching portion 44 is not limited to an annular member equipped with a through-hole 45. For example, it may be, a pin protruding from the cylindrical body 43 toward the outside thereof. In this case, the pin has a diameter that is smaller than the width of the respective notches 42A and 42B.

Figure 8:
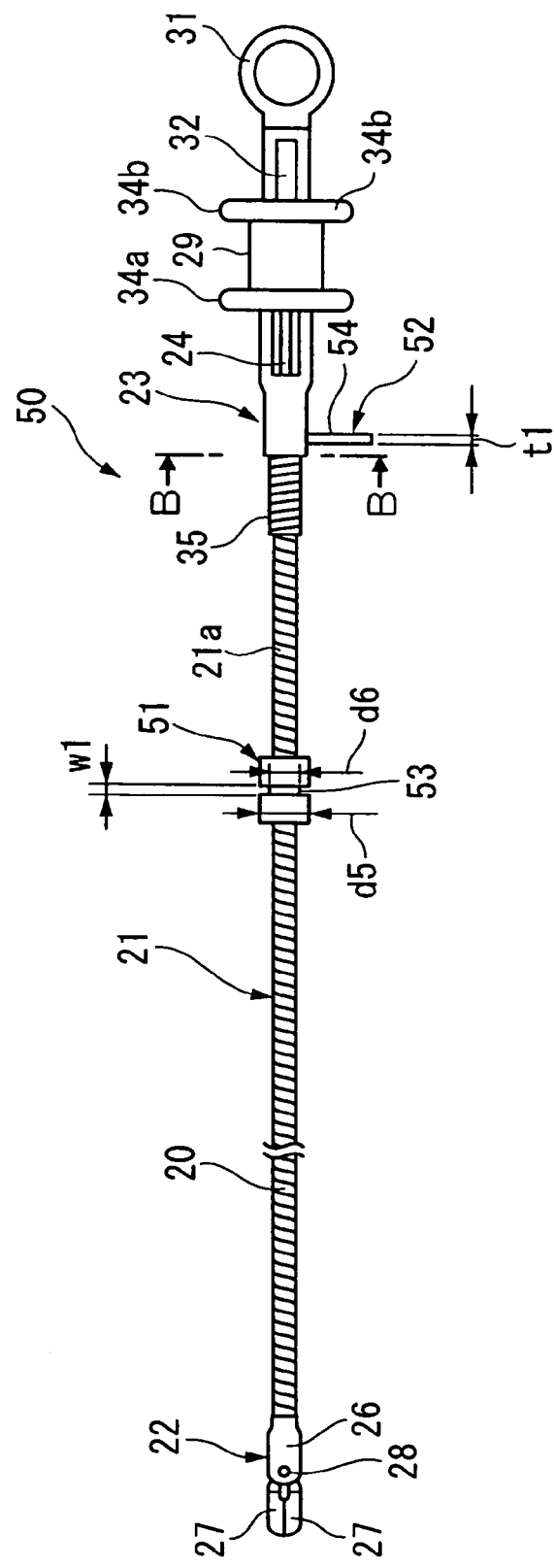
FIG. 8 is a view depicting a configuration of the instrument for an endoscope.
Figure 9:
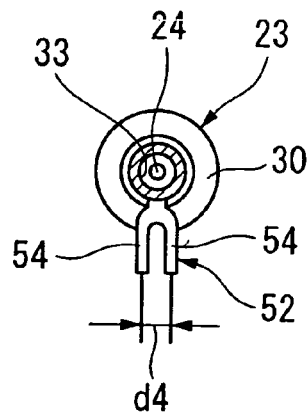
FIG. 9 is a sectional view taken along line B-B of FIG. 8.
Figure 10:
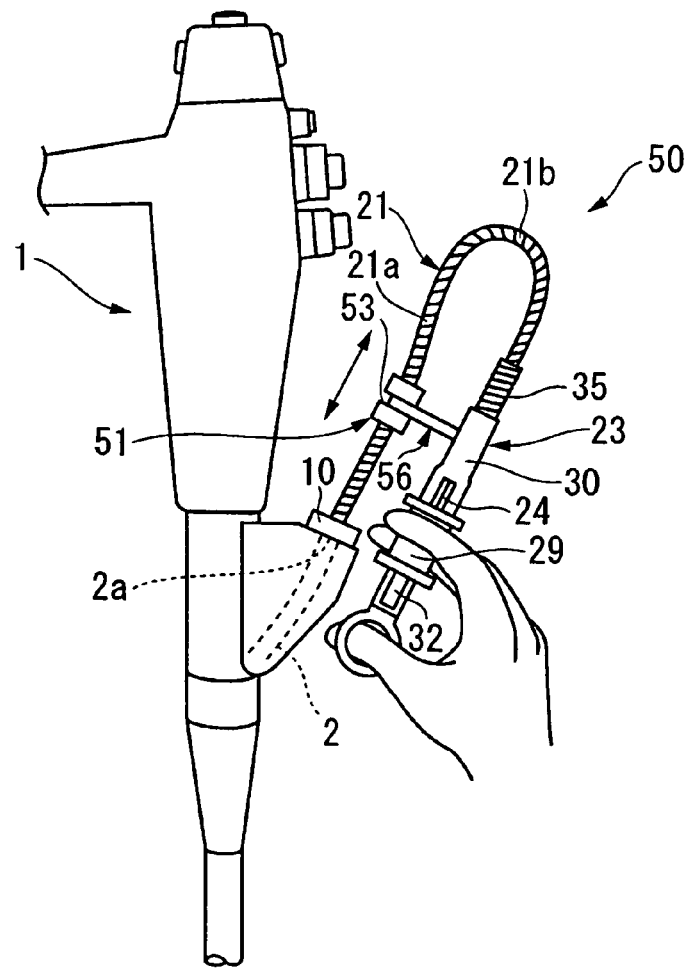
FIG. 10 is a view depicting operation of the instrument for an endoscope.

Next, a description is given of a third embodiment of an instrument for an endoscope according to the present invention with reference to FIG. 8 through FIG. 10. Also, components which are identical to those of the embodiments described above are given the same reference numerals, and redundant description thereof is omitted.

As depicted in FIG. 8, an instrument 50 has an engaged member 51 provided at a part 21a protruding out from the endoscope 1 (refer to FIG. 1), of the insertion portion 21, and has a hook 52 provided on the operation portion body 30 of the operation portion 23. The engaged member 51 and the hook 52 compose the engaging device. The engaged member 51 is made of a cylindrical member encircling the sheath 20 of the insertion portion 21. A ring-shaped groove is provided from the distal end toward the proximal end, wherein the groove is made into a catching portion 53.

The hook 52 is mounted at a predetermined position between the distal end of the operation portion body 30 and the slit 32. The hook 52 extends from the proximal end on the operation portion side 30 side toward the outside of the operation portion body 30. As depicted in FIG. 9, the distal end portion of the hook 52 is notched to make it roughly U-shaped. The width of the notch, that is, the distance d4 between the two engaging pieces 54 is smaller than the outer diameter d5 of the large-diameter portion of the engaged member 51 depicted in FIG. 8, but is larger than the outer diameter d6 of the catching portion 53 which is a small-diameter portion. In addition, as depicted in FIG. 8, the thickness t1 of the engaging piece 54 is lower than the width w1 of the catching portion 53. Further, the thickness t1 of the engaging member 54 corresponds to the length along the length of the operation portion body 30.

A description is given of operation of the instrument 50 with reference to FIG. 8 and FIG. 10. First, after the paired biopsy cups 27 are opened by operating the operation portion 23 in a state where the instrument 50 is inserted into the instrument insertion channel 2, the insertion portion 21 and the operation portion 23 are engaged with each other toward the distal end. That is, the hook 52 is engaged in the catching portion 53 formed between the large-diameter portions of the engaged member 51. In this state, if the operation portion 23 is moved so that the hook 52 is moved toward the instrument insertion channel 2, the engaged member 51 engaged with the hook 52 extends toward the instrument insertion channel 2. At this time, the insertion portion 21 to which the engaged member 51 is fixed also extends into the instrument insertion channel 2, and the treatment portion 22 extends at the distal end of the endoscope equivalent thereto.

When the treatment portion 22 is extended until the biopsy cups 27 are pushed into a predetermined living body tissue, the slider 29 is retracted, and the paired biopsy cups 27 are closed to catch the tissue therebetween. If the operation portion 23 is moved so that the hook 52 is pulled apart from the instrument insertion channel 2, the engaged member 51 engaged with the hook 52 is caused to move. In line therewith, the insertion portion 21 to which the engaged member 51 is fixed is pulled back, the treatment portion 22 in a human body is retracted, and the living body tissue in the biopsy cups 27 is torn.

According to the embodiment, as in the embodiments described above, it is made possible to pull back the treatment portion 22 to outside the human body by engaging the hook 52 with the catching portion 53.

Further, since the catching portion 53 is a groove provided in the engaged member 51, it is possible to move the treatment portion 22 not only in the direction along which the treatment portion 22 is retracted but also in the direction along which the treatment portion 22 is extended without exchanging the hook 52 and the engaged member 51.

Figure 11:
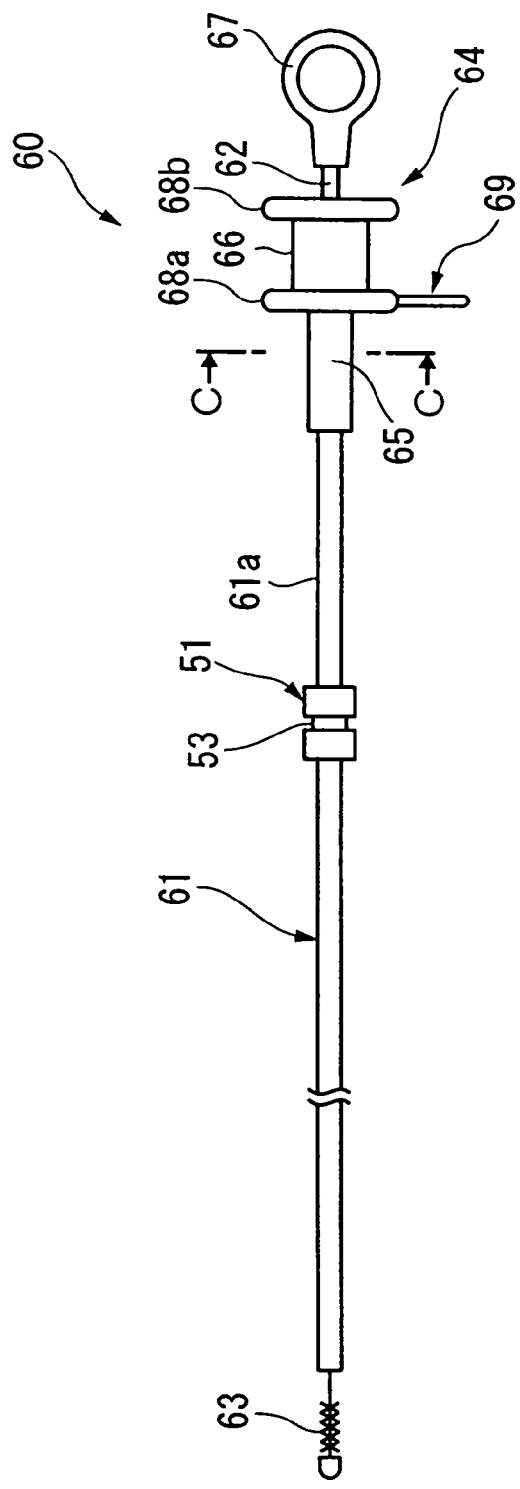
FIG. 11 is a view depicting a configuration of the instrument for an endoscope.
Figure 12:
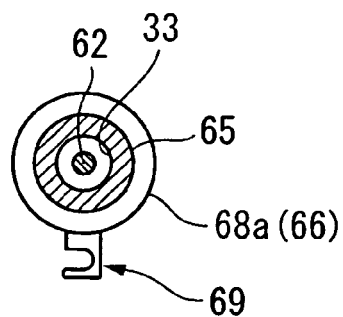
FIG. 12 is a sectional view taken along line C-C of FIG. 11.
Figure 13:
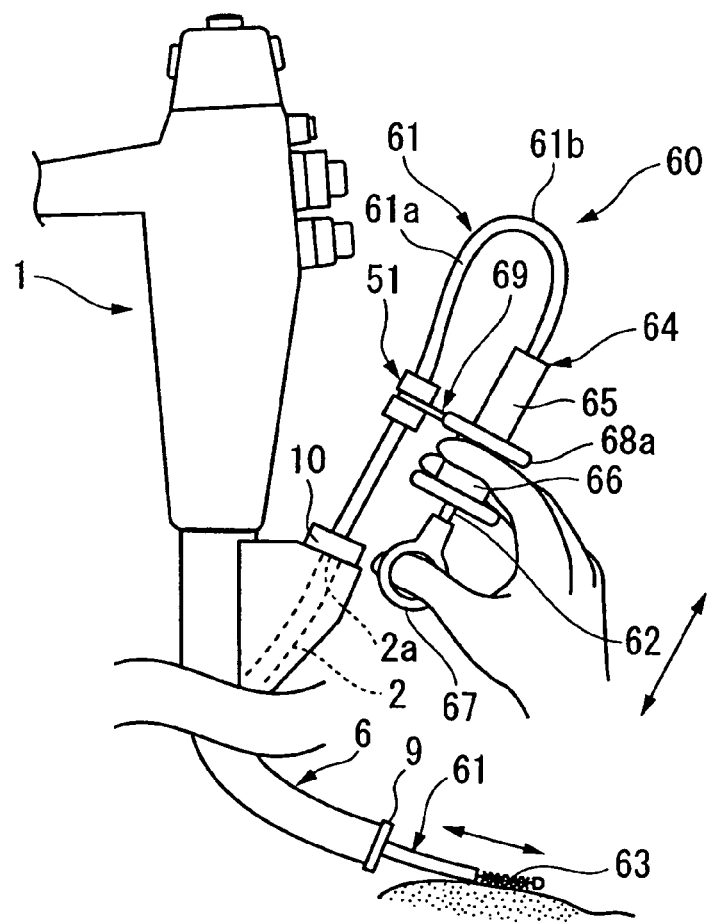
FIG. 13 is a view depicting operation of the instrument for an endoscope.

Next, a description is given of a fourth embodiment of an instrument for an endoscope according to the present invention with reference to FIG. 11 through FIG. 13. Components which are identical to those of the embodiments described above are given the same reference numerals, and redundant description thereof is omitted.

As depicted in FIG. 11, an instrument 60 is a cytological diagnosis brush. The insertion portion 61 of the instrument 60 has flexibility, and an operation wire 62 is inserted into the interior thereof. A brush portion 63 of the instrument is attached to one end of the operation wire 62. The brush portion 63 can be accommodated in the insertion portion 61 when it is not being used. The handle portion 66 of the operation portion 64 is connected to the proximal end of the insertion portion 61. In addition, the vicinity of the proximal end of the insertion portion 61 is covered with a protection member 65 connected to the handle portion 66. Furthermore, the other end of the operation wire 62 passes through the handle portion 66 of the operation portion 64 and is connected to a finger-hook handle 67. The distal end and proximal end of the handle portion 66 are provided with flange portions 68a and 68b having a large outer diameter.

The engaging device of the instrument 60 includes an engaged member 51 attached to a part 61a protruding out from the endoscope 1 (refer to FIG. 13), of the insertion portion 61 and a hook 69 attached to the operation portion 64. The hook 69 has its proximal end attached to the flange portion 68a on the distal side of the handle 67, and extends toward the outside of the handle portion 66. As depicted in FIG. 12, the distal end of the hook 69 is notched from a direction roughly orthogonal to the extension direction of the hook 69. For this reason, the distal end of the hook 69 is formed to be roughly U-shaped in the plan view orthogonal to the length of the operation portion 64. The width of the hook 69 and the size of the notch have dimensions which make it engagable with the catching portion 53 of the engaged member 51.

A description is given of movement of the instrument 60 with reference to FIG. 11 and FIG. 13. First, the finger-hook handle 67 is extended to the handle portion 66 in a state where the instrument 60 is inserted into the instrument insertion channel 2. Thereby, the operation wire 62 connected to the finger-hook handle 67 is pushed out, and the brush portion 63 is projected from the distal end opening of the insertion portion 61. After that, the hook 69 is engaged with the engaged member 51. The operation portion 64 is moved so that the hook 69 is made to approach the forceps port 2a, and so that the hook 69 is kept away from the forceps port 2a. In line therewith, the insertion portion 61 engaged by the hook 69 reciprocates with respect to the instrument insertion channel 2, and the brush portion 63 is extended and retracted with respect to the living body tissue, and the living body tissue is abraded. By pulling back the finger-hook handle 67 after disengaging the hook 69 from the engaged member 51, the brush portion 63 is accommodated in the insertion portion 61. After that, by removing the instrument 60 from the instrument insertion channel 2, tissue adhered to the brush portion 63 can be collected.

According to the embodiment, since the engaged member 52 is provided on a section 61a from the forceps port 2a of the insertion portion 61 to the operation portion 64, and the hook 69 is provided on the distal side from the position where the operation portion 64 is held, it becomes possible to extend and retract the insertion portion 61 and the brush portion 63 while operating the operation portion 64 without directly gripping the insertion portion 61. Therefore, an operator becomes able to carry out operation of the cytological diagnosis brush by way of natural actions. In addition, since it is not necessary to simultaneously grip the operation portion 64 and the insertion portion 61 with the hands, it is possible to prevent stress from being concentrated at the portion 61b (refer to FIG. 13) where the insertion portion 61 is bent, presenting excessive bending of the insertion portion 61.

Figure 14:
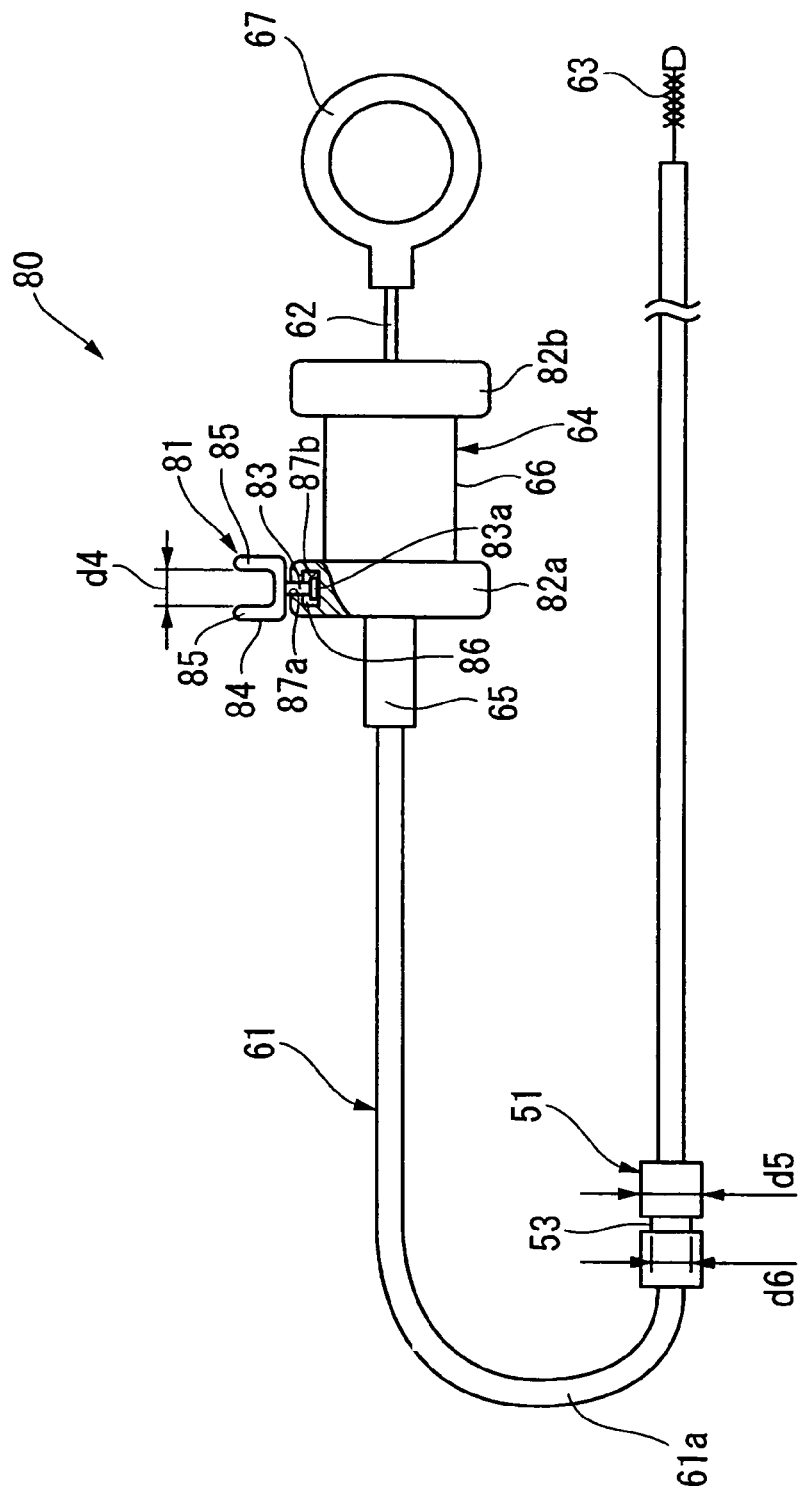
FIG. 14 is a view depicting a configuration of the instrument for an endoscope.
Figure 15:
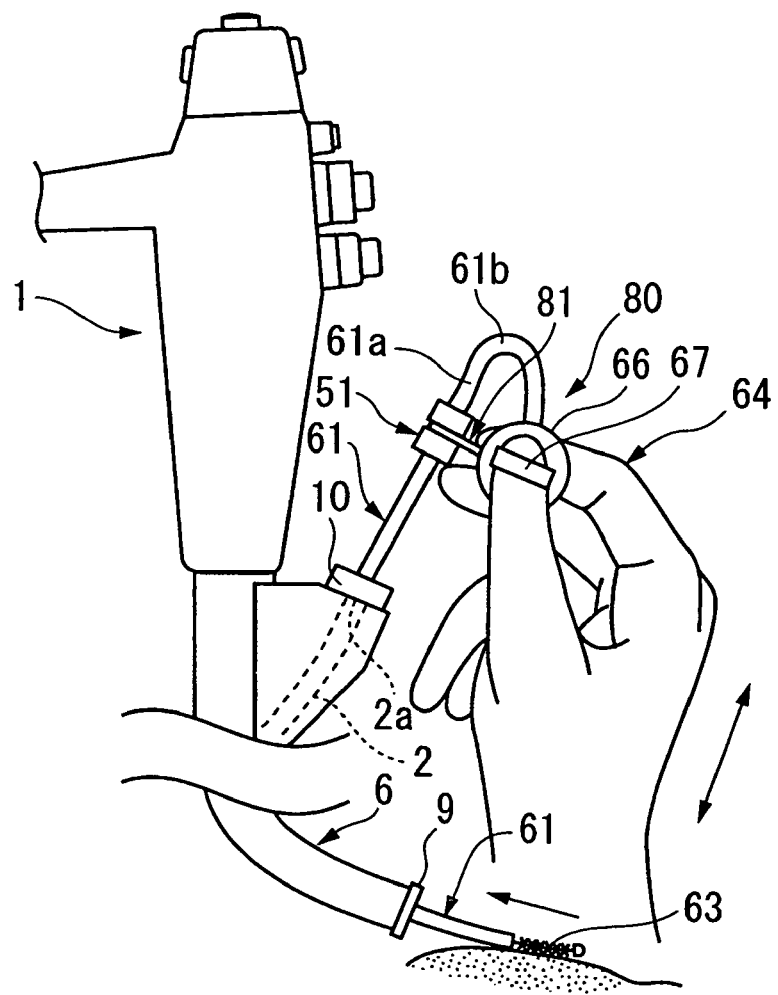
FIG. 15 is a view depicting operation of the instrument for an endoscope, and depicts a state where the insertion portion and the operation portion are engaged with each other in such a way as to be roughly orthogonal to each other.

Next, a description is given of a fifth embodiment of an instrument for an endoscope according to the present invention with reference to FIG. 14 and FIG. 15. Also, components which are identical to those of the embodiments described above are given the same reference numerals, and redundant description thereof is omitted.

As depicted in FIG. 14, an instrument 80 has the engaged member 51 provided on a section 61a protruding out from the endoscope 1 (refer to FIG. 1), of the insertion portion 61 and has a hook 81 rotatably provided on the handle portion 66 of the operation portion 64, and the engaged member 51 and the hook 81 compose the engaging device. The hook 81 consists of a pin 83 a part of which is accommodated in the flange portion 82a of the handle portion 66, and a distal end 84 attached to the distal end of the pin 83. A large-diameter portion whose diameter is enlarged is formed at the proximal end of the pin 83. The distal end 84 is bifurcated by a notch, and two engaging pieces 85 extending parallel to the length of the pin 83 are formed. The distance d4 between the engaging pieces 85 is smaller than the outermost diameter d5 of the engaged member 51, but is larger than the outer diameter d6 of the catching portion 53. In addition, the thickness of the engaging pieces 85 is smaller than the width of the catching portion 53.

The distal end and proximal end of the handle portion 66 which rotatably supports the hook 81 are enlarged, thereby forming a flange portion 82a and a flange portion 82b. Further, the flange portion 82a is provided with an attaching hole 86 for the hook 81. The attaching hole 86 is provided on the outside of the handle portion 66. The width of the opening 87 on the outer surface of the attaching hole 86 is roughly equal to the outer diameter of the pin 83. A portion 87b nearer to the center of the handle portion 66 than the opening portion 87 has a larger inner diameter than the outer diameter of the large-diameter portion 83a of the pin 83. That is, the hook 81 is rotatable around the axis of the pin 83 while slidably bringing the pin 83 in contact with the opening 87a, and disengagement from the handle portion 66 can be prevented by the large-diameter portion 83a.

If the hook 81 is oriented in such an axis as depicted in FIG. 14, that is, in such an axis that the engaging pieces 85 of the hook 81 are disposed along the length of the operation portion 64, the instrument 80 can make the insertion portion 61 engage with the operation portion 64 so that the axis line of the insertion portion 61 in the vicinity of the engaged member 51 is orthogonal to the axis line of the operation portion 64 substantially. Also, if the operation portion 64 is reciprocated so that the engaged member 51 is extended and retracted with respect to the forceps port 2a in a state where the insertion portion 61 and the operation portion 64 are engaged with each other so as to be cross each other, the insertion portion 61 and the brush portion 63 are extended and retracted, living body tissue is abraded.

Thus, if the operation portion 64 is designed so that it can be operated in a posture where it crosses the insertion portion 61, it is possible to carry out operation of the instrument 80 by way of natural actions. In addition, it is possible to securely prevent the operation portion 64 from interfering with the endoscope 1. Also, if the direction of a tip of the hook 81 is established from the direction along which the engaging pieces 85 of the hook 81 are arrayed in the circumferential direction of the operation portion 64, that is, the direction of the tip of the hook 81 depicted in FIG. 14, to the direction in which the engaging pieces 85 are turned by 90° around the center of the pin 83, it is possible to engage the operation portion 64 with the insertion portion 61 roughly parallel to each other as in the fourth embodiment. Furthermore, the orientation of the hook 81 can be set other than as in the two orientations described above. That is, by adjusting the engagement angle of the operation portion 64 with the insertion portion 61 in response to the position of a patient, positions of the endoscope 1 and the instrument 80, and the convenience of an operator, it can be made possible for the operator to easily carry out operation of the endoscope 1 and the instrument 80 alone. In addition, it is possible to prevent load from being concentrated at the curvature portion of the insertion portion 61.

Also, the hook 81 may be composed of a roughly U-shaped member having both ends of the bottom part erected parallel to each other and having a stepped screw. An opening is provided in the bottom surface, and the axis portion of the stepped screw is passed through the opening. Then, the screw portion is tightened to the handle portion 66. The diameter of the opening is roughly equal to the outer diameter of the axis portion of the stepped screw and is smaller than the outer diameter of the head portion, so that it becomes possible to optionally set the rotation angle of the roughly U-shaped member with the stepped screw made into the center of rotation.

Figure 16:
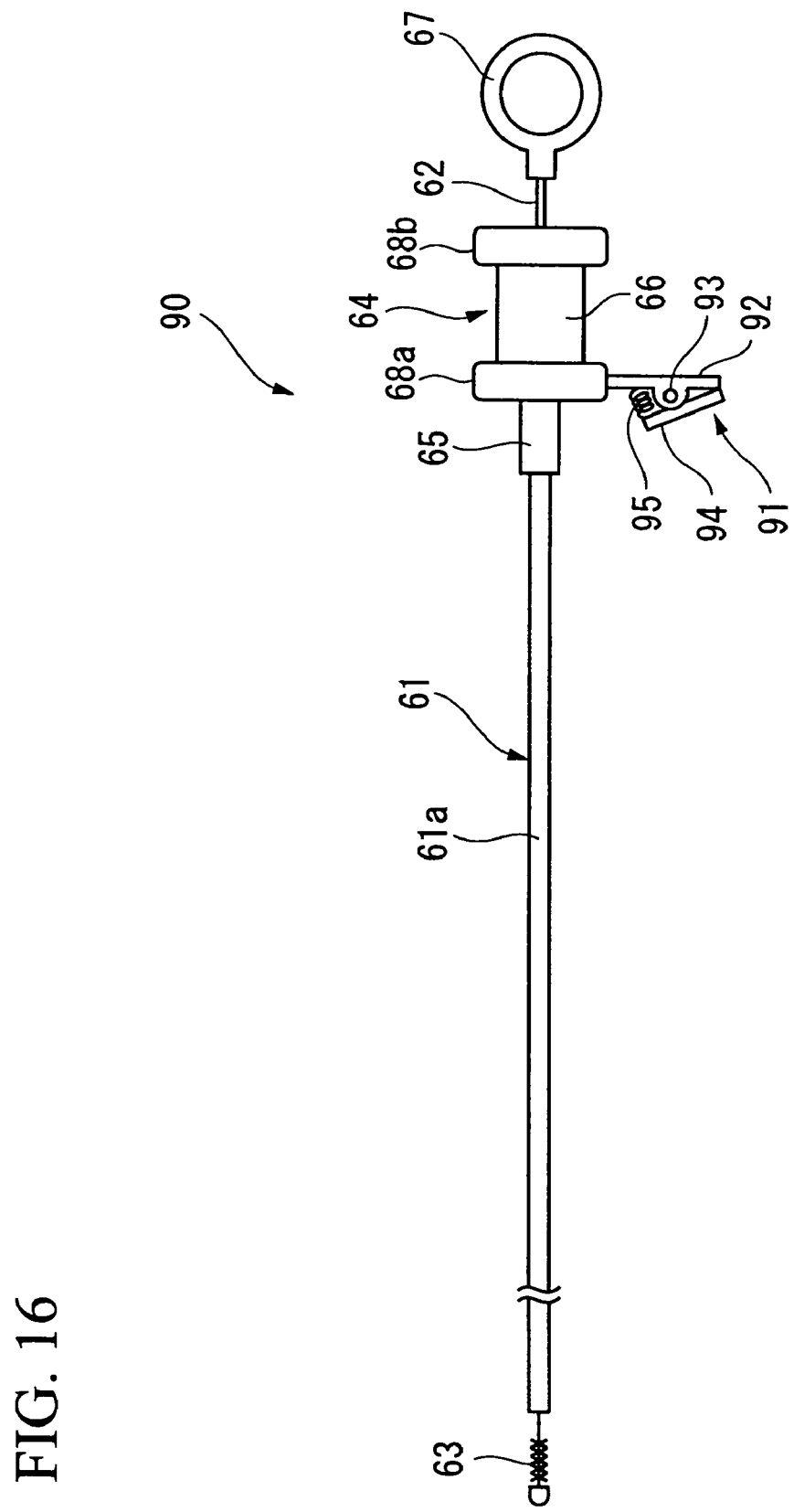
FIG. 16 is a view depicting a configuration of the instrument for an endoscope.

Next, a description is given of a sixth embodiment of an instrument for an endoscope according to the present invention with reference to FIG. 16. Further, components which are identical to those of the embodiments described above are given the same reference numerals, and redundant description thereof is omitted.

As depicted in FIG. 16, the engaging device of the instrument 90 is composed of a gripping member 91 attached to the operation portion. The gripping portion 91 includes a fixing piece 92 fixed at the handle portion 66 of the operation portion 64. The fixing piece 92 is disposed roughly orthogonal to the axial line of the handle portion 66. Further, a pin 93 is fixed between the proximal end, fixed at the handle portion 66, of the fixing piece 92 and the distal end thereof. A rotating piece 94 is rotatably supported by the pin 93. The rotating piece 94 has roughly the same width and thickness as those of the fixing piece 92, and is disposed to align with the fixing piece 92 along the axial line of the operation portion 64. One end of a coil spring 95 as a resilient member is engaged with the proximal end portion from the portion supported by the pin 93 at the rotating piece 94. The other end of the coil spring 95 is engaged with the proximal end portion from the pin 93 of the fixing piece 92. Therefore, the rotating piece 94 is continually pressed so that the distal end portion thereof is brought into contact with the distal end portion of the fixing piece 92 by the coil spring 95.

In the instrument 90, a portion near the forceps port 2*a* (refer to FIG. 13) of the endoscope 1, which is the portion 61 *a* protruding out from the endoscope 1, of the insertion portion 61, is gripped with the same placed between the fixing piece 92 and the rotating piece 94. Therefore, if the operation portion 64 reciprocates, since the insertion portion 61 and the operation portion 64 are engaged so as to cross each other, the insertion portion 61 and the brush portion 63 are extended and retracted.

According to the embodiment, since the operation portion 64 and the insertion portion 61 are reliably engaged with each other by the gripping member 91 gripping the insertion portion 61, it is possible to extend and retract the brush portion 63 easily and reliably. Therefore, it becomes possible for an operator to carry out operation of the endoscope 1 and the instrument 90 alone.

Herein, the fixing piece 92 and the rotating piece 94 may be disposed on the outside of the handle portion 66. In this case, the operation portion 64 and the insertion 61 are engaged with each other roughly parallel to each other.

In addition, the present invention can be widely applied without limitation to the modes according to the embodiments. For example, the instrument 70 according to the third embodiment as depicted in FIG. 8 may be a cytological diagnosis brush. In this case, the treatment portion 22 is made into a brush. Also, the instruments 60, 80 and 90 according to the fourth, fifth and sixth embodiments depicted in FIG. 1 through FIG. 16 may be biopsy forceps. In these cases, the supporting member 26, paired biopsy cups 27, support axis 28 and link mechanism are provided in the treatment portion instead of the brush portion 63.

Further, the instruments 3, 40, 50, 60, 80, and 90 in the embodiments may have a treatment portion equipped with a plurality of resilient gripping members. The proximal ends of the resilient gripping members are connected to the operation wires 24 and 62, and the distal ends thereof are made into claws. The claws of the resilient gripping members protrude from the insertion portions 21 and 61, and are opened and widened when the operation wires 24 and 62 are extended, and are accommodated in the insertion portions 21 and 61 when the operation wires 24 and 62 are retracted, and then grip a target substance. If such instruments are provided with the engaging device, it becomes possible for an operator to easily carry out operation of the treatment portion and to extend and retract the insertion portion alone.

Also, the hook 81 as depicted in FIG. 14 may be fixed the flange portion 82*a*. Instead of the rotatable hook 81 as depicted in FIG. 14, the shape of the engaged member may be changed, and the operation portions 23 and 64 and the insertion portions 21 and 61 may cross each other and engage with each other. For example, with respect to the catching portion 44 as depicted in FIG. 7, the hook 42 may be engaged in such an orientation in which the operation portion 23 and the insertion portion 21 cross each other.

Further, the hooks 36, 42, 52, 69 and 81 may be mounted on the insertion portions 21 and 61, and the catching portions 44 and 53 engaged with the engaged members 25, 41, and 51 or the hooks 36, 42, 52, 69 and 81 may be provided on the operation portions 23 and 64. Also, the gripping member 91 may be provided on the insertion portion 61.

In the instrument for an endoscope according to the present invention, the engaging device allows the part of the insertion portion protruding out from the endoscope to engage with the operation portion. Accordingly, if the operation portion is moved, the insertion portion is pushed in the channel of the endoscope and is pulled out therefrom in interlock with movement of the operation portion. That is, it is possible for an operator to extend and retract the distal end of the insertion portion by only moving his/her hand gripping the operation portion without the assistance of an assistant. Accordingly, it becomes possible for an operator to operate both an endoscope and an instrument alone. Also, the engaging device may be provided only on either one of the operation portion or the insertion portion, or may be provided on both the operation portion and the insertion portion.

In the instrument for an endoscope according to the present invention, since the position of engagement with the insertion portion by the engaging device is forward of the position where the operation portion is held, the insertion portion can be easily extended and retracted in a state where the operation portion and the insertion portion are engaged with each other, and it is possible for an operator to easily operate both the endoscope and the instrument.

In the instrument for an endoscope according to the present invention, for example, in a case where the hook is provided on the operation portion and the engaged member is provided on the insertion portion, the operation portion is made to approach the engaged member, and the hook is engaged with the engaged member. It thus becomes easy to engage the operation portion and the insertion portion with each other and to disengage them from each other by only the hook being caught on or removed from the engaged member. In addition, this is the same where the hook is provided in the insertion portion and the engaged member is provided in the operation portion.

In the instrument for an endoscope according to the present invention, for example, in a case where the first engaging device is provided in the operation portion and the second engaging device is provided in the insertion portion, the operation portion is moved toward the second engaging device along the insertion portion while clipping the insertion portion so as to set the insertion portion in the notched section. If the operation portion is further moved beyond the point at which the first engaging device is brought into contact with the second engaging device, the operation portion is engaged with the insertion portion, and the insertion portion is pushed in the channel of the endoscope or pulled out therefrom in interlock with the engagement. The second engaging device may be provided with a recess coincident with the notched section. Also, this is the same where the second engaging portion is provided in the operation portion and the first engaging device is provided in the insertion portion.

In the instrument for an endoscope according to the present invention, the gripping member grips the insertion portion or the operation portion. For example, where the gripping member is provided in the operation portion, if the insertion portion is gripped by the gripping member, it is possible to extend or retract the distal end of the insertion portion by only moving a hand gripping the operation portion.

In the instrument for an endoscope according to the present invention, it becomes possible for the engaging device to be engaged without unnatural folding of the wrist, and movement of hands for moving the insertion portion becomes natural, and it becomes unlikely that the operation portion will interfere with the endoscope and the like.

As the instrument for an endoscope according to the present invention, an instrument used with the operation of the endoscope so as to move the insertion portion reciprocally while operating the treatment portion, such as the biopsy forceps and cytological diagnosis brush, is included if the instrument is used, it becomes possible for an operator to operate the endoscope and the instrument alone.

According to the present invention, since the engaging device allows the part of the insertion portion protruding out from the endoscope to engage with the operation portion, it is possible for an operator alone to extend and retract the distal end of the insertion portion by only moving the hand gripping the operation portion without the assistance of an assistant. Accordingly, it becomes possible for an operator to operate both the endoscope and the treatment instruction alone.

Some preferred embodiments of the present invention are described above. However, the present invention is not limited to the above-described embodiments. The present invention may be subjected to addition, omission, substitution, and other modifications in the constructions within the scope not departing from the spirit of the present invention. The present invention is not limited by the above description, but is limited only by the scope of the claims attached hereto.

The present invention relates to an instrument for an endoscope, including an insertion portion inserted into the channel of an endoscope; a treatment portion provided at the distal end of the insertion portion for treating a target region; and an operation portion provided at the proximal end of the insertion portion for operating the treatment portion; and further including an engaging device by which a part protruding out from the endoscope, of the insertion portion is engaged with the operation portion. With the instrument for an endoscope according to the present invention, it is possible for an operator to extend and retract the distal end of the insertion portion by only moving a hand gripping the operation portion without the assistance of an assistant, and it is possible for the operator to operate the endoscope and its instrument simply and alone.

What is claimed is:

1. An instrument for an endoscope, the instrument comprising:
    an insertion portion having a distal end, a proximal end and a middle portion between the distal end and the proximal end, and configured to be insertable into a channel of the endoscope;
    a treatment portion configured to treat a target region, wherein the treatment portion is arranged substantially at the distal end of the insertion portion;
    an operation wire which is inserted into the insertion portion, and of which the distal end is connected to the treatment portion so as to operate the treatment portion;
    an operation portion which is disposed at the proximal end of the insertion portion, and which is connected to the proximal end of the operation wire so that the treatment portion is available to be operated by moving the operation wire back and forth; and
    a connecting portion which is configured to connect the operation portion to the middle portion of the insertion portion, wherein the connecting portion comprises:
        an engaged member which is disposed on the insertion portion; and
        a pushing member which is disposed at the operation portion, and which is configured to contact the engaged member in a longitudinal direction of the middle portion of the insertion portion in a state where the operation portion is connected to the middle portion of the insertion portion;
    wherein the pushing member pushes the engaged member while moving the operation portion in the longitudinal direction, and thereby the middle portion of the insertion portion is moved in the longitudinal direction with the pushing member.

2. The instrument for an endoscope according to claim 1, wherein the pushing member comprises a hook provided on the operation portion, and thereby the hook is engaged with the engaged member.

3. The instrument for an endoscope according to claim 1, wherein the connecting portion comprises:
    a first engaging member provided on the operation portion as the pushing member and having a notch, into which the insertion portion is fittable, formed thereon; and
    a second engaging member provided on the insertion portion as the engaged member and having a large-diameter portion formed thereon, whose diameter is larger than the width of the notch.

4. The instrument for an endoscope according to claim 1, wherein the connecting portion allows a part of the insertion portion to engage with the operation portion so that the insertion portion and the operation portion cross each other.

5. The instrument for an endoscope according to claim 1, wherein the operation portion is removably attached to the insertion portion.

6. The instrument for an endoscope according to claim 1, wherein the treatment portion comprises a pair of biopsy cups between which living body tissue may be gripped.

7. The instrument for an endoscope according to claim 1, wherein the treatment portion comprises a brush portion for abrading living body tissue.

8. The instrument for an endoscope according to claim 1, wherein the connection in which the insertion portion is connected with the operation portion via the connecting portion enables to maintain in state where the insertion portion is bent.

9. The instrument for an endoscope according to claim 1, wherein:
    the operation portion comprises:
        a main body which is connected to the proximal end of the insertion portion, and
        a slider to which the operation wire is connected, the slider being configured to be slidable on the main body of the operation portion;
    wherein:
        the slider is moved toward a distal end of the main body, and thereby the operation wire is moved forward, and
        the operation portion is connected to the middle portion of the insertion portion such that the distal end of the main body opposes the distal end of the insertion portion, and thereby the middle portion of the insertion portion is moved in an opposing direction toward the distal end of the insertion portion while moving the operation portion toward the distal end of the main body of the insertion portion.

* * * * *